(12) United States Patent
Knudsen et al.

(10) Patent No.: US 8,470,534 B2
(45) Date of Patent: Jun. 25, 2013

(54) METHODS OF PREDICTING RESISTANCE OR SENSITIVITY TO THERAPIES FOR CANCER

(76) Inventors: Erik S. Knudsen, Wynnewood, PA (US); Emily E. Bosco, Cincinnati, OH (US)

( * ) Notice: Subject to any disclaimer, the term of this patent is extended or adjusted under 35 U.S.C. 154(b) by 670 days.

(21) Appl. No.: 11/949,604

(22) Filed: Dec. 3, 2007

(65) Prior Publication Data
US 2009/0149333 A1 Jun. 11, 2009

Related U.S. Application Data

(60) Provisional application No. 60/872,211, filed on Dec. 1, 2006.

(51) Int. Cl.
*C12Q 1/68* (2006.01)
*C12P 19/34* (2006.01)

(52) U.S. Cl.
USPC .................. 435/6.11; 435/6.12; 435/6.14

(58) Field of Classification Search
None
See application file for complete search history.

(56) References Cited

U.S. PATENT DOCUMENTS

| | | | | |
|---|---|---|---|---|
| 7,622,251 | B2 * | 11/2009 | Baker et al. | 435/6 |
| 2001/0051344 | A1 * | 12/2001 | Shalon et al. | 435/6 |
| 2007/0059720 | A9 * | 3/2007 | Fuqua et al. | 435/6 |

OTHER PUBLICATIONS

Thisted (1998) What is a P-Value. University of Chicago. May 25, 1998. accessed from http://www.stat.uchicago.edu/~thisted. six pages.*
Michiels et al. Lancet, 2005; 365:488-492.*
Slonin, Nature Genetics Supplement, vol. 32, Dec. 2002, pp. 502-508.*
Baker. Journal of the National Cancer Institute, vol. 95, No. 7, Apr. 2, 2003.*
Enard et al (Science. Apr. 12, 2002; 296(5566):340-43).*
Hoshikawa et al (2003) Physiol Genomics 12:209-219, 2003.*
Chen et al. (Molecular and Cellular Proteomics 1:304-313, 2002).*
Hurd et al. Oncogene (1997) 15: 991-995.*
Dowsett. Clinical Cancer Research, Jan. 2003, vol. 9, 502S-510S.*
Ma et al. (Cancer Cell: Jun. 2004; vol. 5, pp. 607-616).*
Bosco. 2001. dissertation submitted to the Division of Research and Advanced Studies of the University of Cincinnati, May 8, 2006. 158 pages.*
Howell et al., The Lancet, vol. 345, Issue 8971, p. 29-30.*
Inoue et al., J. of Molecular Endocrinology(2002), vol. 29, p. 175-192.*
Howell et al., (1995) The Lancet, vol. 345, Issue 8971, p. 29-30.*
Oh et al., Molecular Endocrinology (2001), vol. 15: 1344-1359.*
Osborne et al, British Journal of Cancer (2004), vol. 90, S2-S6.*
Massarweh et al., Endocrine-Related Cancer (2006), 13, S15-S24.*
Nemere et al, Journal of Cellular Biochemistry(2003), 88, p. 438-445.*
Riggins et al. Molecular Cancer Therapeutics(2005), 4(1), p. 33-41.*
Hirsch et al., Mol. Cell. Biol. Dec. 2000 vol. 20, p. 9182-9191.*

* cited by examiner

*Primary Examiner* — Juliet Switzer
(74) *Attorney, Agent, or Firm* — Dinsmore & Shohl LLP

(57) ABSTRACT

The present application is directed to methods of predicting the resistance of a tumor to molecularly targeted therapy and methods of predicting sensitivity of a tumor to DNA damaging therapy. The methods include: a) determining the level of expression of plurality of genes regulated by retinoblastoma tumor supressor (RB) in the individual, and b) comparing the level of expression of the plurality of genes regulated by RB in the individual with a level of expression of the plurality of genes regulated by RB in a control. The application is also directed to an RNA expression profile for the loss of RB.

9 Claims, 9 Drawing Sheets
(2 of 9 Drawing Sheet(s) Filed in Color)

METHODS OF PREDICTING RESISTANCE OR SENSITIVITY TO THERAPIES FOR CANCER

CROSS-REFERENCES TO RELATED APPLICATIONS

This application claims the benefit of U.S. Provisional Application No. 60/872,211, filed Dec. 1, 2006, which is incorporated herein by reference.

FIELD

The present invention is directed to methods of predicting resistance or sensitivity to therapies for cancer and to RNA expression profiles.

BACKGROUND

It has been speculated that within five years, cancer will surpass heart disease as the leading cause of death. Presently, one in three people will contract cancer, and one in four will die from the disease. Since 1950, the overall cancer incidence has increased by 44 percent; the incidence of breast cancer and male colon cancer by about 60 percent; testis, prostate and kidney by 100 percent; and other cancers, such as malignant melanoma, multiple myeloma and some lymphomas, by over 100 percent. Often, cancer is treated with a doctor's best guest as to what will be the most effective therapy and cancer regiments change with the outcome of the trial and error. Thus, ways to predict responses to cancer treatments are needed.

SUMMARY

One embodiment of the present invention is directed to a method of predicting the resistance of a tumor to molecularly targeted therapy. The method includes: a) determining the level of expression of a plurality of genes regulated by retinoblastoma tumor suppressor (RB) in the individual, and b) comparing the level of expression of the plurality of genes regulated by RB in the individual with a level of expression of the plurality of genes regulated by RB in a control, wherein the control represents a tumor responsive or non-responsive to the therapy; wherein, for a control representing a tumor responsive to the therapy, a higher expression of the plurality of genes regulated by RB in the individual as compared with the control predicts resistance to the therapy, and for a control representing a tumor resistant to the therapy, a similar level of expression of the plurality of genes regulated by RB in the individual as compared with the control predicts resistance to the therapy.

Another embodiment is directed to a method of predicting the sensitivity of a tumor to a DNA damaging therapy. The method includes: a) determining the level of expression of a plurality of genes regulated by RB in the individual, and b) comparing the level of expression of the plurality of genes regulated by RB in the individual with a level of expression of the plurality of genes regulated by RB in a control, wherein the control represents a tumor responsive or non-responsive to the therapy; wherein, for a control representing a tumor responsive to the therapy, a similar level expression of the plurality of genes regulated by RB in the individual as compared with the control predicts sensitivity to the therapy, and for a control representing a tumor resistant to the therapy, a higher expression of the plurality of genes regulated by RB in the individual as compared with the control predicts sensitivity to the therapy.

An additional embodiment is directed to a breast cancer RNA expression profile, including, RAD21, BRCA1, ECT2, KIF11, SMC4L1, TOPBP1, STK6, KIF20A, CDC25C, CCNB1, CDC20, CDCA8, KIF2G, BIRC5, CDC45L, CDCA3, PRC1, CCN82, MK167, RAD51, CDCA5, BRRN1, TTK, KIF23, BUB1, CENPA, CCNA2, RRM2, TRIP13, EZH2, MAD2L1, TOP2A, RAD51AP1, TYMS, PCNA, HMGB2, FEN1, NEK2, CKS2, CHEK1, CDC6, GMNN, FIGNL1, TMPO, TCF19, LIG1, MCM2, MCM3, TCF19, BUB1, BRCA2, SMC2L1, PRIM1, RFC5, CDK2, CDCA7, PLTP, TYRO3, or a combination thereof.

Additional embodiments, objects and advantages of the invention will become more fully apparent in the detailed description below.

BRIEF DESCRIPTION OF THE DRAWINGS

The patent or application file contains at least one drawing executed in color. Copies of this patent or patent application publication with color drawings will be provided by the Office upon request and payment of the necessary fee. The following detailed description will be more fully understood in view of the drawings in which.

Figure 1A:
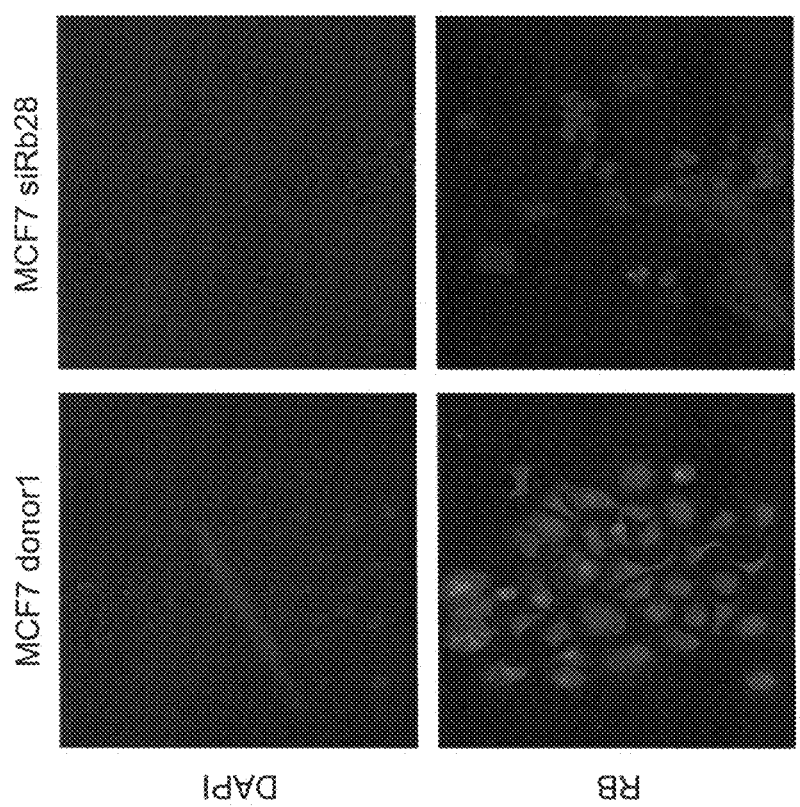
FIG. 1 shows efficient retinoblastoma (RB) knockdown in breast cancer cells causes deregulation of RB/E2F target genes and increased proliferation kinetics: (A) MCF7 cells transfected with MSCV donor or MSCV siRB plasmids are selected with puromycin to isolate stable clones and the clones are screened by RB immunofluorescence as shown for MCF7 donor 1 and siRb28; (B) lysates from MF7 donor 1 and siRb28 clones are immunoblotted for expression levels of RB, PCNA, MCM7, cyclin E, cyclin A, cyclin D1, and p116INK4a where Cdk4 serves as a loading control; (C) cells represented in A are BrdU labeled for 10 hours, and BrdU immunofluorescence is performed and scored; (D) cells represented in A are seeded at $3 \times 10^5$, cell growth assays are carried out for 9 days, and cells are counted every 3 days; (E) lysates represented in B along with lysates from polyclonal populations of T47D and Zr-75-1 cells are infected with retrovirus encoding donor or siRb88 plasmids are immunoblotted for expression levels of RB and cyclin D1, where Lamin B serves as a loading control; and (F) retrovirally infected T47D and Zr-75-1 cells represented in E are seeded at $3 \times 10^5$, and growth assays are carried out as described for D.

The embodiments set forth in the drawings are illustrative in nature and are not intended to be limiting of the invention defined by the claims. Moreover, individual features of the drawings and the invention will be more fully apparent and understood in view of the detailed description.

DETAILED DESCRIPTION

The retinoblastoma tumor suppressor (RB) is a potent inhibitor of cell cycle progression that was initially identified based on bi-allelic inactivation in the pediatric cancer retinoblastoma. Many subsequent studies have demonstrated that RB function is compromised in a large fraction of human cancers which is consistent with the model that deregulation of cell cycle control is a requisite component of tumorigenesis. Owing to widespread inactivation of RB in cancer, the mechanism underlying tumor suppression has been the subject of intense scrutiny.

A critical function of RB is the regulation of gene expression. The RB protein has weak, non-specific, DNA-binding activity. However, RB interacts strongly with a number of sequence specific DNA-binding transcription factors. Among these factors, the best understood is the E2F family of transcription factors. Generally, E2F functions as a heterodimer comprised of E2F and DP subunits. These factors interact with DNA elements in the promoters of a large number of cell cycle regulatory genes as determined by microarray-based gene expression. Specifically, E2F complexes have been attributed to the appropriate control of DNA replication, DNA repair, apoptosis and G2/M regulation. Most of the E2F family members harbor transcriptional activation domains and stimulate the expression of target genes. By interacting with E2F proteins, RB masks the transcriptional activation domains of these proteins. Additionally, RB functions to recruit corepressor activities to functionally repress E2F-mediated gene expression. Thus, activation of RB represses the expression of E2F-regulated genes and mediates the inhibition of cell cycle progression.

To mediate physiological proliferation, RB activity is regulated during cell cycle progression. Mitogenic signaling cascades stimulate the activity of cyclin-dependent kinase (CDK) complexes, which phosphorylate RB. This phosphorylation attenuates the interaction of RB with E2F family members. Thus, as cells progress through the cell cycle, RB-mediated repression is alleviated, and it is believed that this event is critical for cell cycle progression. During tumorigenesis, RB is functionally inactivated through a multitude of mechanisms. Strikingly, these disparate mechanisms all impinge on RB-mediated repression of transcription by disrupting the interaction with E2F and corepressors. Therefore, functional inactivation of RB facilitates the hyperplastic proliferation associated with tumorigenesis.

Additionally, the loss of function or inactivation of RB affects how tumors will react when treated with certain types of therapy, and therefore, affects how doctors will treat their patients. Take, for example, breast cancer. Breast cancer is the leading noncutaneous cancer diagnosis in American women, affecting more than 240,000 new patients per year. Treatment options for breast cancer are governed by the estrogen dependence of the tumor cells. Two-thirds of all breast cancers are estrogen receptor (ER) positive, and in these tumors ER serves as a molecular target for hormone ablation therapy. Antiestrogens, such as the widely used tamoxifen (Tam), are the first-line therapy for ER-positive tumors and efficiently elicit a $G_0/G_1$-phase arrest in hormone-dependent cancer cells. This class of drugs is initially effective in curbing the growth of ER-positive tumors; however, many patients whose tumors initially respond to antiestrogen treatment develop cellular resistance to Tam while maintaining ER-positive disease. This shows that genetic lesions downstream of ER bypass the effectiveness of the therapy. Second-line therapies for tumors that exhibit resistance to antiestrogens have traditionally included radiation and chemotherapies that function by damaging DNA (e.g., cis-platin).

As stated above, the retinoblastoma tumor suppressor (RB) plays a central role in cell-cycle control and regulates the cellular response to diverse therapeutic agents. In quiescent cells, RB is hypophosphorylated and assembles transcriptional repressor complexes on the promoters of E2F-regulated genes to block cell-cycle progression. In response to mitogenic factors, including estrogen in breast cancer cells, RB is inactivated through hyperphosphorylation catalyzed by the cyclin D-cyclin-dependent kinase 4 (cyclin D-cdk4) and cyclin E-cdk2 complexes. These modifications are sufficient to disrupt the interaction of RB with E2F proteins, thereby relieving transcriptional repression and permitting cell-cycle progression. In contrast, antimitogenic factors activate RB, inhibiting cell-cycle progression. For example, RB activity is instrumental in the DNA damage-induced cell-cycle checkpoint and is necessary for G1- and S-phase arrest following DNA-damaging events. Correspondingly, Tam and other antiestrogens function to block RB phosphorylation and engage RB-mediated transcriptional repression of E2F.

RB has been reported to be aberrant in approximately 20%-35% of breast cancers and has been associated with poor disease outcome. Additionally, loss of heterozygosity or other alterations at the Rb locus are routinely observed in primary breast cancer specimens. Furthermore, the overproduction of cyclin D1 and cyclin E, which mediate the inactivation of RB, are relatively common events in breast cancer. Lastly, microarray analyses has indicated that deregulation of E2F target genes can be associated with poor prognosis in a very specific subset of breast cancer cases. In this regard, there is clear evidence for context-dependent effects of RB, which would have implications for the therapeutic strategies employed.

Resistance to conventional therapy is one of the main causes of patient death associated with breast cancer. Given the frequent disruption of RB function in breast cancer, the effect of this event upon the response to therapeutic agents is imperative for the optimal design of treatment strategies. Here, RB knockdown in breast cancer cells resulted in deregulation of E2F-regulated genes and a growth advantage in vitro, which was recapitulated by accelerated tumor development in xenograft models. The effect of RB knockdown was determined in the context of radiation, cisplatin (cis-diamminedichloroplatinum II [CCDP]), or hormone ablation therapy. RB deficiency enabled cells to inappropriately progress through the cell cycle following challenge with all therapeutic modalities tested. In the context of DNA-damaging therapeutics, RB deficiency increased therapeutic sensitivity in both cell culture and xenograft models. In contrast, following Tam therapy, the bypass of cell-cycle inhibition enabled proliferation in the presence of therapy and corresponding therapeutic failure in xenograft models. Similar to RB deficiency, ectopic expression of E2F3 bypassed the cell-cycle arrest mediated by therapeutic agents, suggesting that deregulated E2F activity underlies the changes in therapeutic response in RB-deficient breast cancer cells. Using a signature of 59 RB-regulated genes to probe microarray data from breast cancer patients tested with Tam, it was revealed that highly elevated gene expression levels correlated with failure of Tam therapy. Together, these results demonstrate that aberrations in RB facilitate accelerated tumorigenic proliferation of breast cancer cells and differential response to 2 major breast cancer treatment modalities.

Therefore, in one embodiment, the present application is directed to a method of predicting the resistance of a tumor to molecularly targeted therapy. The method includes: a) determining the level of expression of a plurality of genes regulated by RB in the individual, and b) comparing the level of expression of the plurality of genes regulated by RB in the individual with a level of expression of the plurality of genes regulated by RB in a control, wherein the control represents a tumor responsive or non-responsive to the therapy; wherein, for a control representing a tumor responsive to the therapy, a higher expression of the plurality of genes regulated by RB in the individual as compared with the control predicts resistance to the therapy, and for a control representing a tumor resistant to the therapy, a similar level of expression of the plurality of genes regulated by RB in the individual as compared with the control predicts resistance to the therapy.

In one embodiment, the control represents a retrospective cohort of tumors responsive or non-responsive to the therapy. In one embodiment, the higher expression is defined as being 2 fold higher, and in a more specific embodiment as being 3 fold higher, in the individual than in the control. In another embodiment, determining the level of expression of plurality of genes regulated by RB in the individual includes determining the level of expressed RNA of the plurality of genes regulated by RB in the individual. In a further embodiment, the RNA levels are determined by microarray analysis, quantitative polymerase chain reaction, or a combination thereof. The level of expression of the plurality of genes regulated by RB in the control is determined previously or simultaneously in a similar manner.

In one embodiment, determining the level of expression of plurality of genes regulated by RB in the individual comprises determining the level of expressed proteins of the plurality of genes regulated by RB in the individual, for example using quantitative immunohistochemistry. The level of expression of the plurality of genes regulated by RB in the control is determined previously or simultaneously in a similar manner.

In another embodiment, the tumor is caused by a cancer which inactivates retinoblastomoma tumor suppressor. In a further embodiment, the cancer comprises breast cancer, prostate cancer, liver cancer, lung cancer or combinations thereof. In an even further embodiment, the molecularly targeted therapy comprises hormonal therapy, for example antiestrogen or antiandrogen therapy, or an agent such as iressa gleevac, or the like. In one embodiment, the antiestrogen therapy comprises tamoxifen, faslodex, an aromatase inhibitor, raloxifene, or a combination thereof.

The plurality of genes upregulated by E2F comprises at least 2 such genes. In a more specific embodiment, the plurality comprises at least 10 such genes, and in a more specific embodiment, the plurality comprises at least 20 such genes. In another embodiment, the plurality comprises at least 100 such genes, and in a further embodiment, the plurality comprises about 140 such genes. See, for example, Markey et al, *Oncogene*, 2007 Sep. 20; 26(43):6307-18, incorporated herein by reference. In another embodiment, the plurality of genes upregulated by E2F is upregulated in the absence of retinoblastoma tumor suppressor. In a further embodiment, the plurality of genes regulated by RB is selected from the group consisting of: RAD21, BRCA1, ECT2, KIF11, SMC4L1, TOPBP1, STK6, KIF20A, CDC25C, CCNB1, CDC20, CDCA8, KIF2G, BIRC5, CDC45L, CDCA3, PRC1, CCN82, MK167, RAD51, CDCA5, BRRN1, TTK, KIF23, BUB1, CENPA, CCNA2, RRM2, TRIP13, EZH2, MAD2L1, TOP2A, RAD51AP1, TYMS, PCNA, HMGB2, FEN1, NEK2, CKS2, CHEK1, CDC6, GMNN, FIGNL1, TMPO, TCF19, LIG1, MCM2, MCM3, TCF19, BUB1, BRCA2, SMC2L1, PRIM1, RFC5, CDK2, CDCA7, PLTP, TYRO3, or a combination thereof. In another embodiment, determining the level of expression of the plurality of genes regulated by RB in the individual comprises determining the average level of expression of a plurality of genes regulated by RB in the individual. The level of expression of the plurality of genes regulated by RB in the control may similarly involve determining the average level of expression of a plurality of genes regulated by RB in the control.

Another embodiment is directed to a method of predicting the sensitivity of a tumor to a DNA damaging therapy. The method includes: a) determining the level of expression of a plurality of genes regulated by RB in the individual, and b) comparing the level of expression of the plurality of genes regulated by RB in the individual with a level of expression of the plurality of genes regulated by RB in a control, wherein the control represents a tumor responsive or non-responsive to the therapy; wherein, for a control representing a tumor responsive to the therapy, a similar level expression of the plurality of genes regulated by RB in the individual as compared with the control predicts sensitivity to the therapy, and for a control representing a tumor resistant to the therapy, a higher expression of the plurality of genes regulated by RB in the individual as compared with the control predicts sensitivity to the therapy.

The plurality of genes upregulated by E2F comprises at least 2 such genes. In a more specific embodiment, the plurality comprises at least 10 such genes, and in a more specific embodiment, the plurality comprises at least 20 such genes. In another embodiment, the plurality comprises at least 100 such genes, and in a further embodiment, the plurality comprises about 140 such genes. See, for example, Markey et al, *Oncogene*, 2007 Sep. 20; 26(43):6307-18, incorporated herein by reference. In another embodiment, the plurality of genes upregulated by E2F is upregulated in the absence of retinoblastoma tumor suppressor. In a further embodiment, the plurality of genes regulated by RB is selected from the group consisting of: RAD21, BRCA1, ECT2, KIF11, SMC4L1, TOPBP1, STK6, KIF20A, CDC25C, CCNB1, CDC20, CDCA8, KIF2G, BIRC5, CDC45L, CDCA3, PRC1, CCN82, MK167, RAD51, CDCA5, BRRN1, TTK, KIF23, BUB1, CENPA, CCNA2, RRM2, TRIP13, EZH2, MAD2L1, TOP2A, RAD51AP1, TYMS, PCNA, HMGB2, FEN1, NEK2, CKS2, CHEK1, CDC6, GMNN, FIGNL1, TMPO, TCF19, LIG1, MCM2, MCM3, TCF19, BUB1, BRCA2, SMC2L1, PRIM1, RFC5, CDK2, CDCA7, PLTP, TYRO3, or a combination thereof. In another embodiment, determining the level of expression of the plurality of genes regulated by RB in the individual comprises determining the average level of expression of a plurality of genes regulated by RB in the individual. The level of expression of the plurality of genes regulated by RB in the control may similarly involve determining the average level of expression of a plurality of genes regulated by RB in the control.

In one embodiment, the tumor is caused by a cancer which inactivates retinoblastoma tumor suppressor. In a further embodiment, the cancer includes: breast cancer, prostate cancer, liver cancer, lung cancer or a combination thereof.

In a specific embodiment of the present methods, the control may comprise one or more tumors with known responsiveness to molecularly targeted therapy and/or sensitivity to DNA-damaging therapy.

An additional embodiment is directed to an RNA expression profile for loss of RB, including, RAD21, BRCA1, ECT2, KIF11, SMC4L1, TOPBP1, STK6, KIF20A, CDC25C, CCNB1, CDC20, CDCA8, KIF2G, BIRC5, CDC45L, CDCA3, PRC1, CCN82, MK167, RAD51, CDCA5, BRRN1, TTK, KIF23, BUB1, CENPA, CCNA2, RRM2, TRIP13, EZH2, MAD2L1, TOP2A, RAD51AP1, TYMS, PCNA, HMGB2, FEN1, NEK2, CKS2, CHEK1, CDC6, GMNN, FIGNL1, TMPO, TCF19, LIG1, MCM2, MCM3, TCF19, BUB1, BRCA2, SMC2L1, PRIM1, RFC5, CDK2, CDCA7, PLTP, TYRO3, or a combination thereof.

EXAMPLES

Figure 1B:
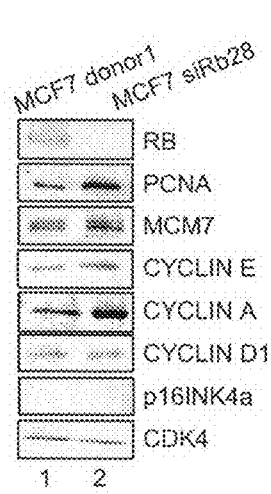

To investigate the influence of RB function in breast cancer, its expression in the ER-positive and estrogen-dependent breast cancer cell line MCF7 is targeted. Specific and stable knockdown of RB is achieved using a vector encoding shRNA directed against Rb. Multiple independent clones transfected with either the short hairpin RNA (shRNA) against Rb or vector control are isolated. RB protein levels are determined using immunofluorescence and immunoblotting for RB (FIGS. 1A and 1B, top panel). These results demonstrate that RB protein levels have been reduced to virtually undetectable levels, and hence the cells are considered RB deficient. Since it has been postulated that nearly all cancer cells harbor compromised RB function, we initially determined the consequence of RB deficiency on E2F target gene expression. Thus, levels of the well-documented RB/E2F targets proliferating cell nuclear antigen (PCNA), minichromosome maintenance 7 (MCM7), cyclin E, and cyclin A are evaluated by immunoblotting. The expression levels of all of these proteins are increased in the absence of RB. However, the levels of cyclin D1 and p 61NK4a (reported to be lost MCF7 cells) are not affected by the reduction in RB protein levels (FIG. 1B).

Figure 1C:
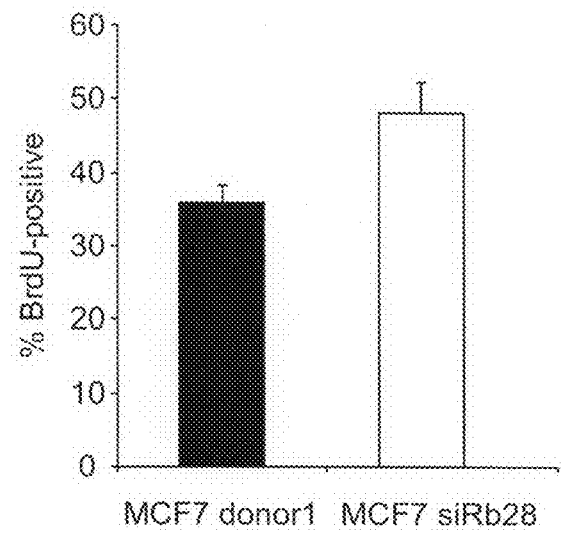
Figure 1D:
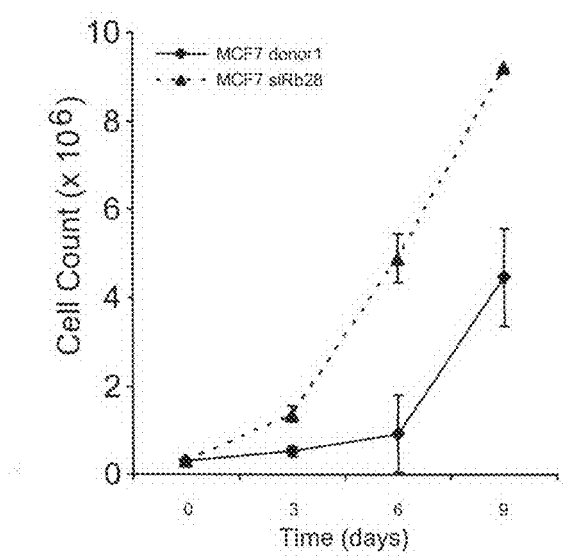
Figure 1E:
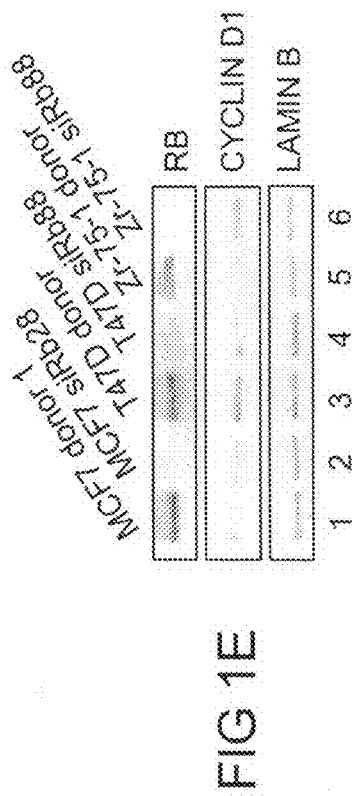
Figure 1F:
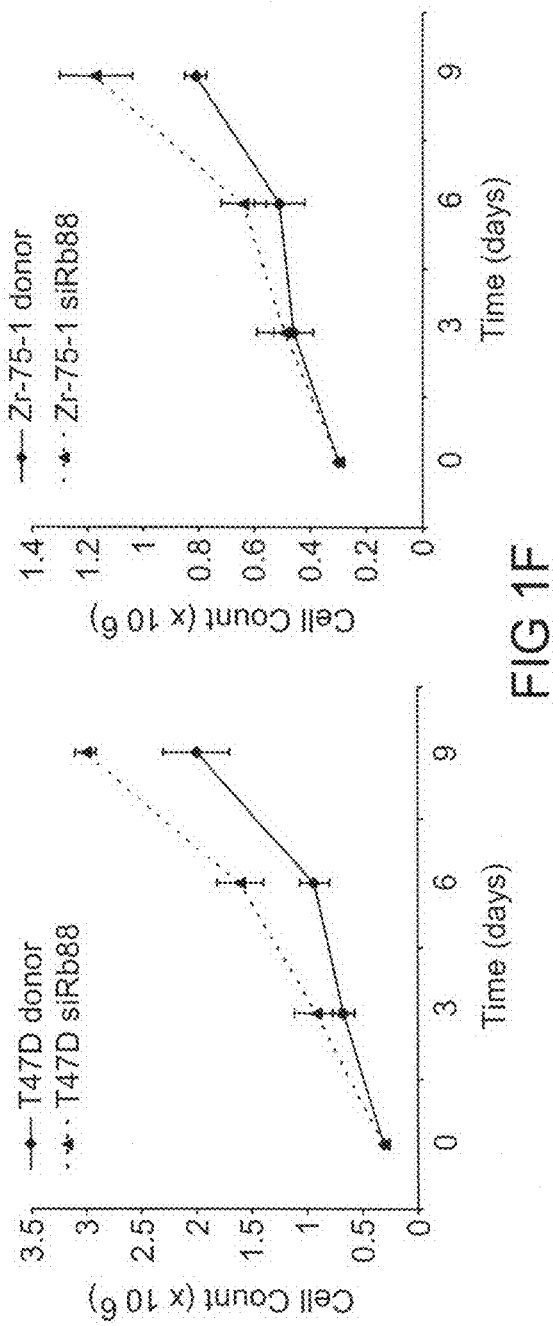

Analyses of cell-cycle progression by BrdU incorporation (FIG. 1C) or cellular proliferation (FIG. 1D) demonstrates that knockdown of RB results in enhanced proliferation. To determine the role of RB in the growth kinetics of additional estrogen-dependent breast cancer cell lines, RB-proficient and -deficient polyclonal pools of both T47D and Zr-75-1 cells are established by infection with retroviruses encoding either an shRNA directed against Rb or control plasmid. RB protein levels are diminished in these cell lines to a level comparable to those evident in the clonal MCF7siRb cells, as determined by immunoblotting. As in MCF7 cells, cyclin D1 levels are unaffected by RB deficiency in T47D and Zr-75-1 cells (FIG. 1E). Importantly, RB knockdown also conferred increased growth kinetics in these cell lines (FIG. 1F). Thus, attenuation of RB alters the proliferative kinetics of established breast cancer cells.

Figure 2:
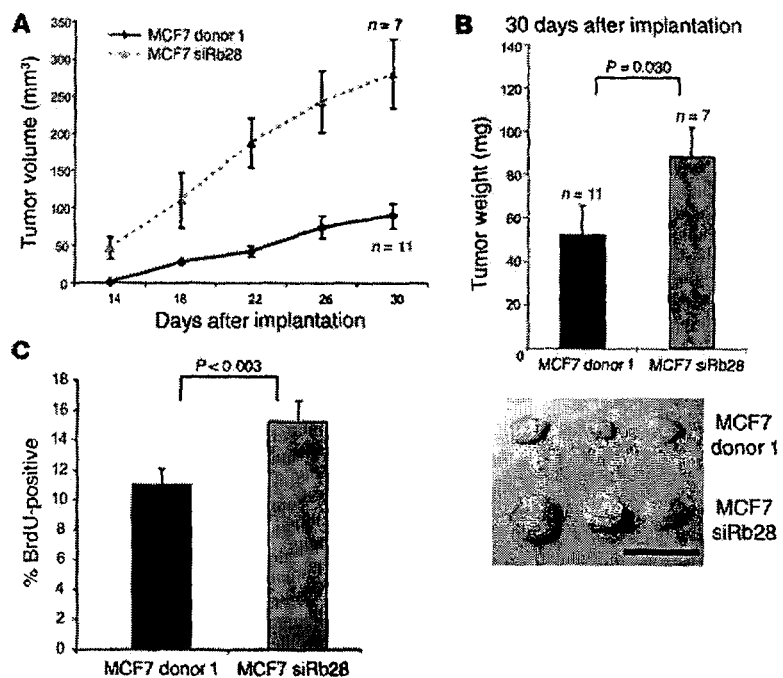
FIG. 2 shows tumor growth in nude mouse xenografts is accelerated in RB knockdown cells: (A) MCF7 donor 1 or siRb28 cells are harvested and resuspended in 3:1 PBS/Matrigel mixture and $2 \times 10^6$ cells in 150 µl of mixture are injected subcutaneously in a contralateral manner in flanks of ovariectomized nude mice, the mice are implanted with E2 pellets and tumors are measured every 4 days; (B) excised tumors are weighed 30 days after implantation, tumor weights are plotted, and a 2-tailed t test assuming unequal variances is used to determine significance; and (C) nude mice represented in A are injected with BrdU 1 hour prior to sacrifice, sectioned tumors are immunohistochemically stained and scored for BrdU incorporation, and statistical analyses is carried out as described for B.

To investigate the biological consequence of RB inactivation in tumorigenesis, nude mouse xenografts are utilized. RB-proficient and -deficient MCF7 cells ($2 \times 10^6$) are injected contra-laterally into the flanks of nude mice implanted with estrogen pellets to support tumor growth. RB-knockdown cells produce measurable tumors earlier than the controls and continue to grow significantly faster (FIG. 2A), so that by 30 days the RB-knockdown tumors has grown to more than double the size of the control tumors. At this time, mice are injected with BrdU and euthanized. Tumors are excised and weighed (FIG. 2B), confirming their larger size. Additionally, BrdU immunohistochemistry demonstrates that the proliferative index is significantly higher in the RB-deficient tumors (FIG. 2C). Thus, even in the context of an established breast cancer cell line, RB plays a pivotal role in modulating tumorigenic proliferation.

Figure 3:
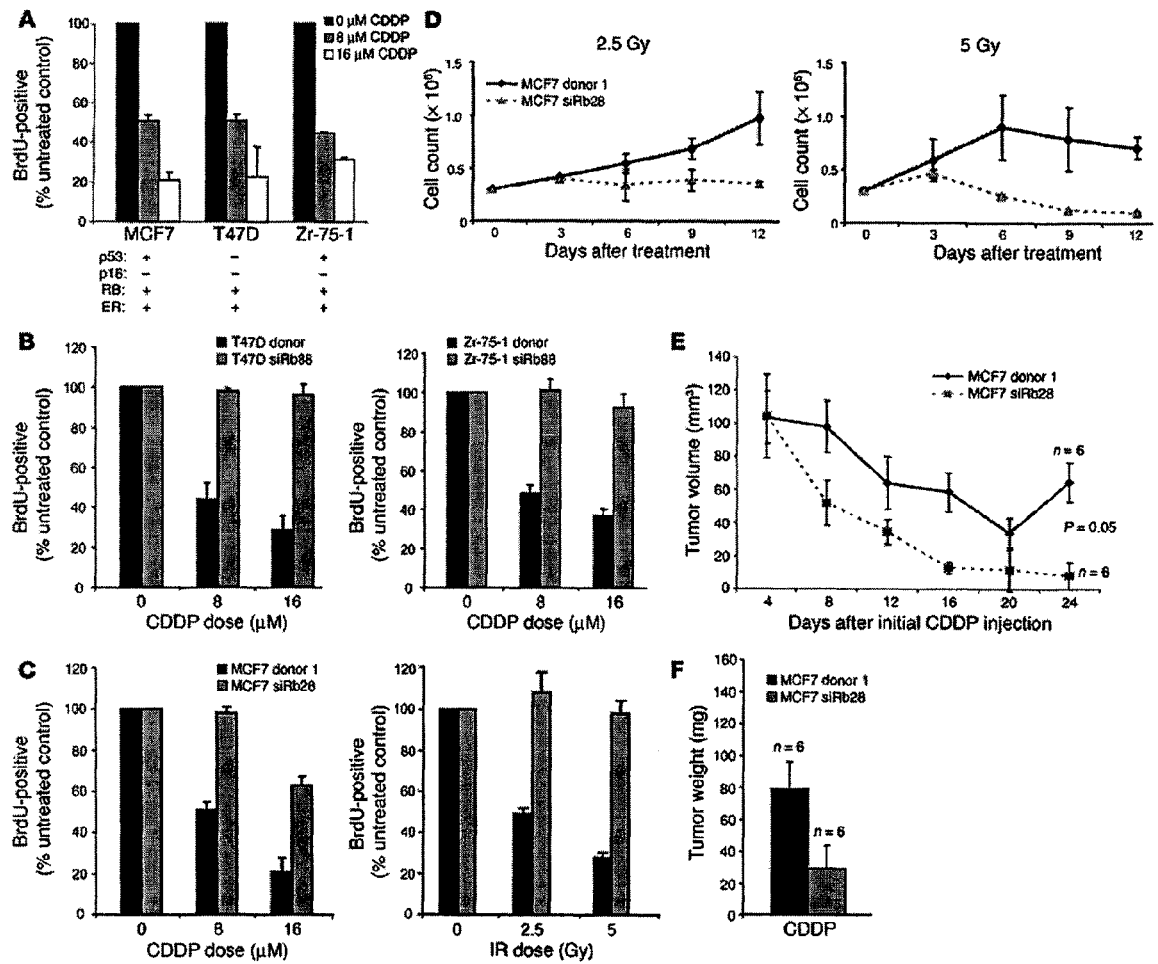
FIG. 3 shows RB deficiency enables bypass of the DNA damage checkpoint, resulting in increased sensitivity: (A) wild-type MCF7, T47D, and Zr-75-1 cells are treated with 0, 8, or 16 µM CDDP for 18 hours, washed, and labeled with BrdU for 10 hours in culture, fixed, and BrdU immunofluorescence is performed and scored; (B) retrovirally infected T47D (left) and Zr-75-1 (right) donor and siRB88 cells are treated with 0, 8, or 16 µM CDDP and BrdU labeled as described for A; (C) MCF7 donor 1 and siRb28 clones are treated with 0, 8, or 15 µM CDDP for 18 hours prior to washing (left) or with 0, 2.5, or 5 Gy IR (right) and BrdU labeled as before; (D) MCF7 donor 1 or siRb28 cells are seeded at $3 \times 10^5$ and treated with 2.5 (left) or 5 Gy IR (right), and cell growth assays are performed for 12 days and cells counted every 3 days; (E) harvested MCF7 donor 1 and siRb28 cells are resuspended 3:1 in PBS/Matrigel and injected subcutaneously into the flanks of mice implanted with E2 pellets, when xenograft tumors reach approximately 110 mm$^3$ during tumor development, mice are treated with CDDP (retain E2 pellet and inject 5 mg/kg CDDP IP every 4 days×5, and tumor size is monitored by caliper measurement) tumor measurements are plotted, and a 2-tailed t test assuming unequal variances is used to determine significance of curves; and (F) tumors represented in E are weighed upon excision.

The RB and p53 tumor suppressors are known to be critical for induction of DNA damage checkpoints, and therapies inducing DNA damage are used as an additional line of treatment for ER-positive breast cancers resistant to hormonal therapy. Therefore, the role of these tumor suppressors in the response to therapeutic doses of DNA-damaging agents is investigated. Wild-type MCF7, T47D, and Zr-75-1 cells are treated with 0, 8, or 16 µM CDDP and labeled with BRDU to determine the effect of the agent on cell-cycle progression. Although these RB-positive cell types differ in p53 status, all cell lines exhibit a dose-dependent cell-cycle checkpoint in response to CDDP treatment (FIG. 3A). To specifically probe the impact of RB in the response to DNA damage, T47D and Zr-75-1 polyclonal donor and siRb88 cells are utilized. These studies demonstrate that RB-proficient T47D and Zr-75-1 cells initiate a dose-dependent checkpoint after CDDP treatment, whereas RB-deficient cells continue to incorporate BrdU efficiently following DNA damage (FIG. 3B). To confirm these findings, MCF7 donor 1 and siRb28 cells are treated with either CDDP as described above or with 0, 2.5, or 5 Gy ionizing radiation (IR). Similarly, these studies reveal that RB deficiency promotes bypass of the DNA damage checkpoints induced by both CDDP and IR treatment in MCF7 cells (FIG. 3C). To determine the long-term effect of DNA damage therapy upon proliferation, cell growth assays are performed wherein the RB-proficient and deficient MCF7 clones are plated at equal density and treated with 2.5 or Gy IR. Cell counting over 12 days revealed that the RB-knockdown cells are more sensitive to IR following treatment with 2.5 and 5 Gy. These data demonstrate that the ability of the eRB-knockdown cells to progress through the cell cycle in the presence of DNA damage is associated with increased sensitivity to these agents.

Further studies of p53 function are carried out in the MCF7 RB-proficient and—deficient clones infected with either empty retroviral vector, LXSN, or LXSN-p53d, an N-terminally truncated, dominant-negative form of murine p53. Immunoblots reveal an accumulation of p53 evident in LXSN-p53dd-infected cells as compared with controls; however, these elevated levels are not associated with an increase in p21 following exposure to 16 µM CDDP for 18 hours, suggesting that p53 function had been effectively compromised. These studies reveal that p53 dysfunction does not impact normal cell proliferation, but it does compromise the DNA damage checkpoint similarly to RB deficiency. Additionally, p53 function did not significantly affect the long-term sensitivity to DNA damage imparted by IR, suggesting that RB is a more critical determinant of the therapeutic response to these types of therapies in this context.

The xenograft model system is then utilized to test the response of RB-deficient tumors to CDDP therapy. Tumors are developed in the flanks of mice by injecting MCF7 donor or siRb cells into the flanks of mice and implanting a 17µ-estradiol (E2) pellet into the back. When tumors reached 100-110 mm$^3$, mice received 5 mg/kg CDDP every 4 days for 5 courses. These experiments revealed that both tumor types regressed during CDDP treatment; however, the RB-deficient tumors regressed more rapidly throughout the 5 courses of therapy (FIG. 3E) and failed to demonstrate any recovery following the completion of therapy. Upon excision, all tumors lacking RB function weigh less than half as much as control tumors following CDDP therapy (FIG. 3F), indicating that RB-deficient tumors respond more favorably to DNA damage therapy.

Figure 4:
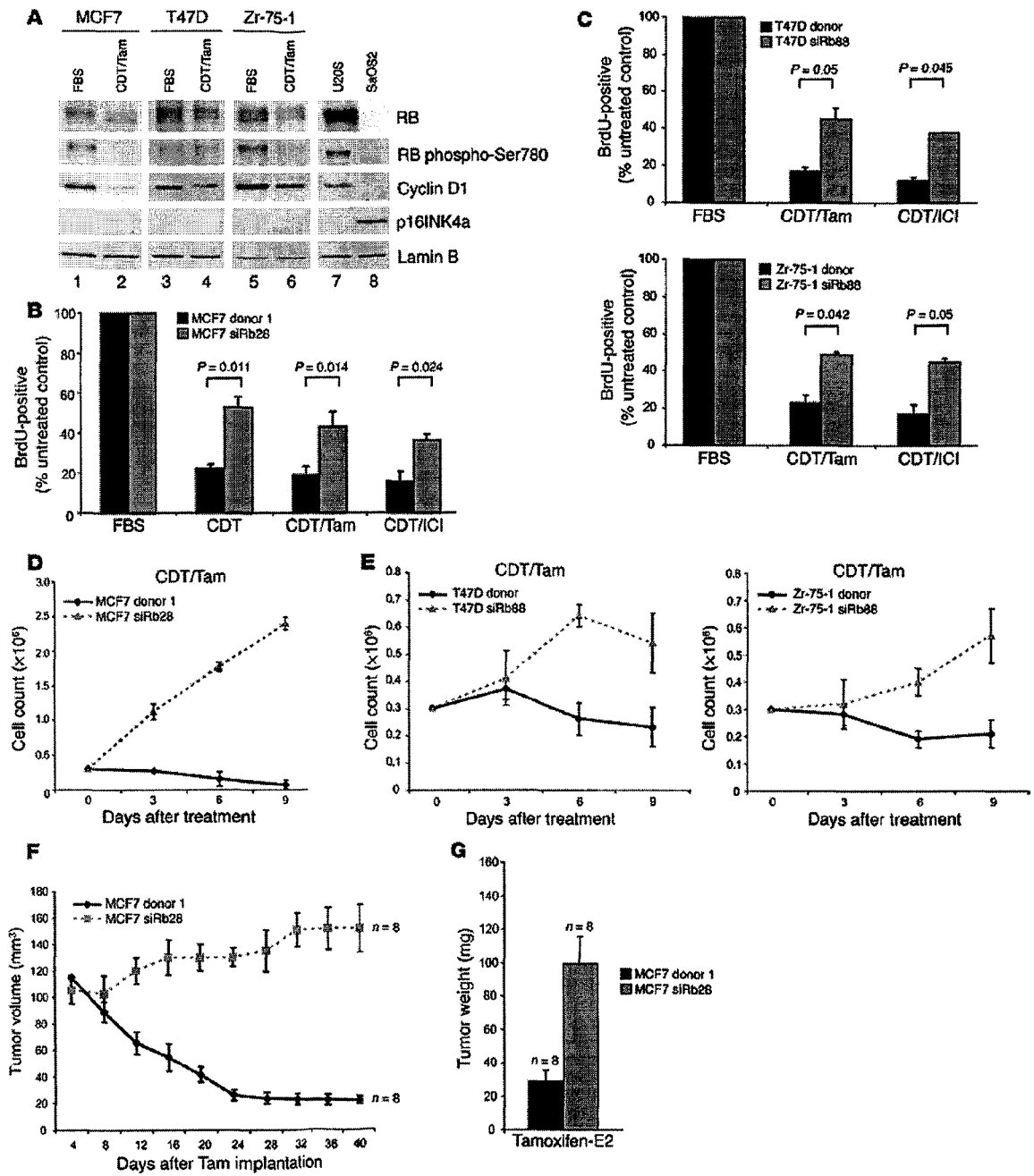
FIG. 4 shows RB is necessary for sensitivity to antiestrogen therapy and long-term growth arrest: (A) lysates from wild-type MCF7, T47D and Zr-75-1 cells are immunoblotted for the expression levels of RB, RB phospho-Ser780, cyclin D1, and p16INK4a, Lamin B serves as a loading control, while lysates from U2OS and SaOS2 cells are included as controls for RB and p16INK4a expression, respectively; (B) MCF7 donor 1 and siRb28 clones are cultured in media containing FBS, CDT, CDT/Tam, or CDT/ICI for 3 days, while BrdU labeling for the final 10 hours, cells are then fixed, and BrdU immunofluorescence is performed and scored; (C) T47D (left) and Zr-75-1 (right) donor and siRb88 cells are cultured, BrdU labeled, scored, and statistical tests are performed as described for B; (D) MCF7 donor 1 or siRb28 cells are seeded at $3 \times 10^5$, and cell growth assays are performed for 9 days while cells are cultured in CDT/Tam and counted every 3 days; (E) T47D (left) and Zr-75-1 (right) donor and siRb88 cells are seeded at $3 \times 10^5$, and cell growth assays are performed as described for D; (F) when xenograft tumors (as in FIG. 3E) reach 100-120 mm$^3$, mice are treated with Tam (remove E2 pellet, add Tam pellet) and tumor size of the Tam-treated animals was monitored by calipers; and (G) final tumor weights of all tumors represented in F upon excision.

RB-deficient cells are able to bypass estrogen ablation therapy. To determine the effect of first-line breast cancer antiestrogen therapies on RB function, cells are exposed to several therapeutically relevant conditions. Specifically, wild-type MCF7, T47D, and Zr-75-1 cells are cultured in medium containing either FBS or charcoal dextran-treated (CDT) serum in addition to Tam, so as to antagonize ER function. In all cell lines, cyclin D1 levels decreased following 72 hours of hormone deprivation, yielding RB dephosphorylation despite undetectable levels of p16INK4a. U20S and SaOS2 cells are included as controls for RB and PI 61NK4a expression levels, respectively (FIG. 4a).

To understand the impact of RB deficiency on the response to hormone deprivation therapy, cells are cultured in CDT, CDT/Tam, or in the presence of pure antiestrogen, ICI182780 (CDT/ICI). Following treatment with these modalities, cells are labeled with BrdU to determine the influence of each agent on cell-cycle progression and the corresponding influence of RB knockdown on this response (FIG. 4B). These experiments are recapitulated in the polyclonal populations of T47D and Zr-75-1 donor and siRb88 cells (FIG. 4C). All conditions limiting estrogen function elicit cell-cycle inhibition in cells harboring functional RB. However, this action of each agent is significantly reduced by the depletion of RB. These results indicate that RB-deficient cells are able to partially bypass the cell-cycle blockade elicited by antiestrogen therapy. To elucidate the long-term growth effects of these therapies, cell proliferation assays are performed over 9 days. RB-proficient and -deficient MCF7 cells are seeded at equal densities and cultured in CDT/Tam (FIG. 4D). As previously described, control MCF7 cells did not exhibit cell proliferation. However, cells lacking RB are able to continue to proliferate in this hormone-deprived environment. Similar results are evident in the same experiments with both T47D and Zr-75-1 RB-proficient and -deficient polyclonal pools (FIG. 4E).

To assess the role of RB in the therapeutic response of MCF7 cells in vivo, the xenograft model is again employed. Upon the attainment of tumors of approximately 100-120 mm$^3$, mice are deprived of estrogen and treated with Tam. Tumor measurements taken at 4-day intervals demonstrate that RB-proficient tumors respond to Tam by regressing to nearly immeasurable sizes. (FIG. 4F). However, the RB-deficient counterparts did not regress and, indeed, increased in size from approximately 10 in mm$^3$ to 150 mm$^3$ in the presence of Tam. All tumors are weighed upon exclusion, and RB-deficient tumors are more than 3 times heavier than control tumors following Tam therapy (FIG. 4G). Together, these data demonstrate that hormone deprivation therapy is compromised in breast cancers harboring functional inactivation of the RB pathway.

Figure 5:
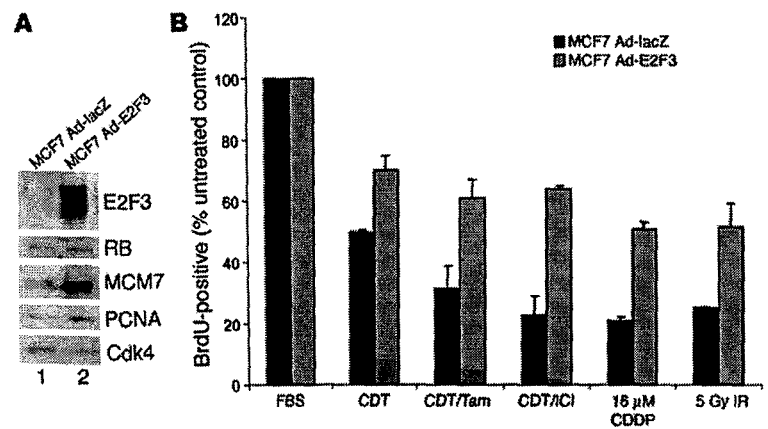
FIG. 5 shows E2F3 overexpression in MCF7 cells allows bypass of antimitogenic checkpoints: (A) MCF7 cells infected with adenoviral vectors encoding either lacZ or E2F3 are harvested 3 days after infection, lysed, separated by SDS-PAGE, and immunoblotted for determination of E2F3, RB, MCM7, and PCNA expression levels, while Cdk4 served as a loading control; and (B) the adenovirus-infected cells represented in A are cultured in media containing FBS, CDT, CDT/Tam, or CDT/ICI for 3 days or are treated as described above with 16 µM CDDP or 5 Gy IR prior to BrdU labeling for 10 hours, cells are then fixed, and BrdU immunofluorescence and scoring are performed.

RB target gene upregulation is a prognostic indicator in human breast cancers. RB performs a myriad of functions, the most well understood being repression of the E2F family of transcription factors. To determine the specific influence of the E2F axis on bypassing therapy, an activator E2F is overexpressed in wild-type MCF7 cells. Specifically, cells are infected either with an adenovirus encoding E2F3 (ad-E2F3) or a control virus (Ad-LacZ) and are harvested 3 days after infection for immunoblot analysis of levels of known RB-E2F targets (FIG. 5A). Relative to control (lane 1), the Ad-E2F3-infected MCF7 cells (lane 2) exhibit significantly increased protein levels of E2F target genes, including PCNA and MCM7. As expected, no changes are detected in RB levels, and CDK4 serves as a loading control. In order to assess the response to therapeutic intervention, 3 days after infection Ad-E2F3- or AdLacZ-infected MCF7 cells are separated into 2 major treatment groups: hormone therapy and DNA damage therapy. The estrogen ablation group is then cultured in the absence of estrogen and in the presence of Tam and ICI as described above. Alternatively, the cells in the DNA damage therapy group are treated with 16 μM CDDP for 18 hours prior to washing or treatment with 5 Gy IR. Cells from both therapy groups are BrdU labeled, and the replicative fraction of treated cells is determined with respect to untreated control cells (FIG. 5B). Cells overexpressing E2F3 exhibit significantly reduced levels of cell-cycle arrest in each therapeutic condition as compared with the control infected cells. This result indicates that the ability of RB-deficient breast cancer cells to bypass therapeutic cell-cycle arrest is due to unrestrained E2F activity, suggesting that RB/E2F-regulated target gene expression is an important marker of therapeutic response.

Figure 6A:
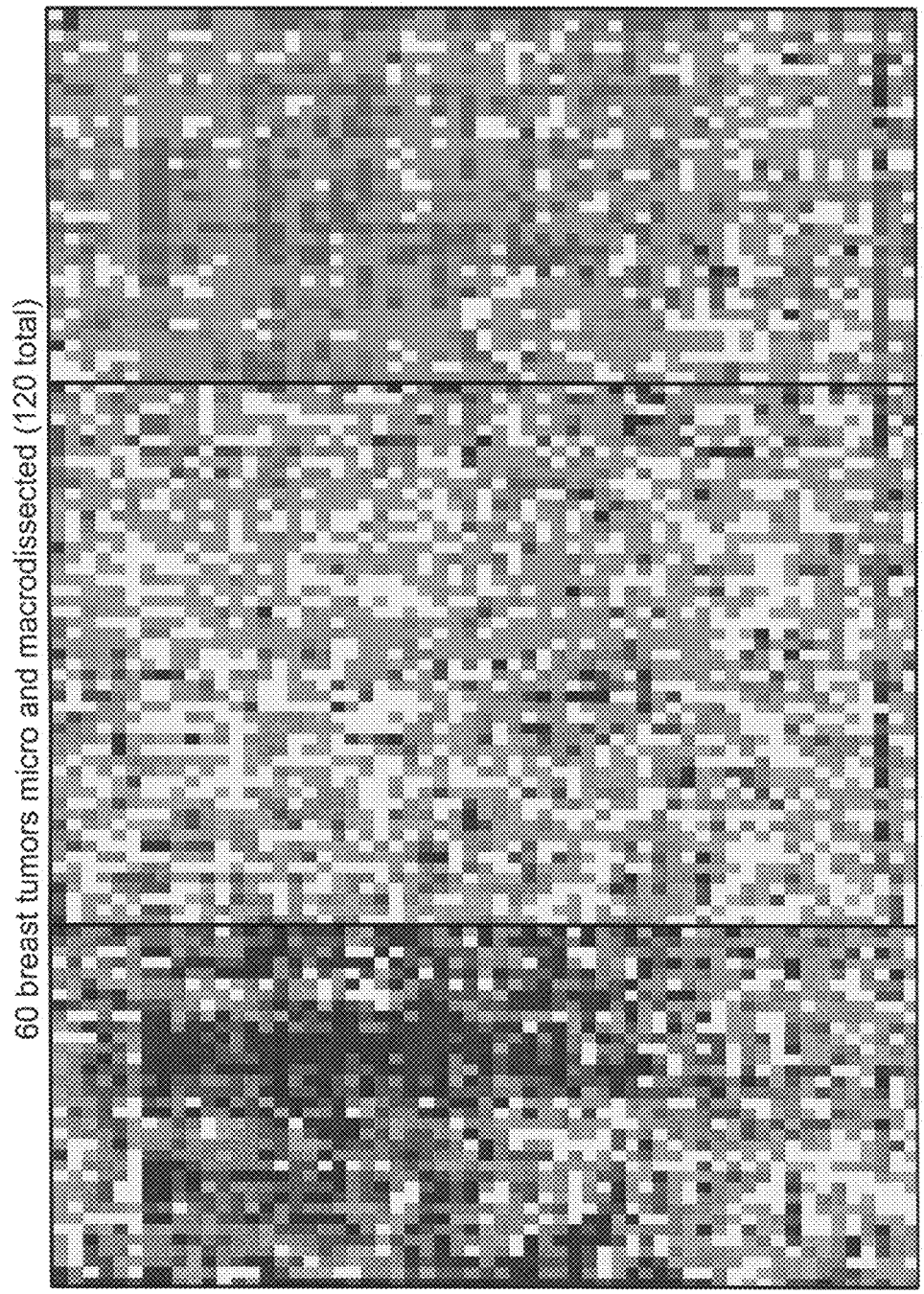
FIG. 6 shows RB/E2F downstream target deregulation correlates with poor prognosis in human breast cancers treated with Tam monotherapy: (A) gene expression data from 60 ER-positive human breast tumors that are both micro- and macrodissected are analyzed for Rb/E2F target gene expression using GeneSpring, where the expression patterns of 59 known RB/E2F target genes and the expression levels of Rb, p16, cyclin D1 and cyclin E are displayed in a condition tree for each of the 2 tissue samples from each patient (120 samples), the average RB/E2F target gene expression levels of all 59 genes are categorized into 3 groups: low, medium, and high and three HER2/neu-positive tumors existed in this tumor set; (B) the RB/E2F target gene expression levels in each group represented in C are averaged and displayed as a box-and-whisker plot, where a 2-tailed t test assuming unequal variances is utilized to determine significance ($P=7.2 \times 10^{-12}$ low/medium; $P=1.3 \times 10^{-14}$ medium/high); and (C) the survival data for each of the 60 patients from the low/medium and high gene expression groups represented in C is compiled into a disease-free survival curve where statistical tests are performed as described for B.

To determine the significance of RB/E2F target gene expression in human breast cancer, a tumor microarray data set representing 60 breast cancer patients with ER-positive disease who are treated with Tam monotherapy is analyzed. The tumor specimens in all cases are both micro- and macrodissected. A gene expression signature of 59 genes that are deregulated with RB genetic loss and repressed upon RB activation is utilized to cluster this 120-point data set (60 tumors, macro- and microdissected) and is displayed as a condition tree (FIG. 6A). This map shows 3 major regions of gene co-regulation: low, medium, and high RB target gene expression (blue, yellow, and red regions, respectively). This clustering placed the macro- and micro-dissected samples from 59 of 60 patients in the same gene expression groups, with only 1 tumor signature split between the high and medium gene expression groups on the condition tree.

First, correlations of the RB gene signature with known effectors of breast cancer growth or development are assessed for relevance to the RB signature. Only 3 tumors within the cohort exhibit HER2/neu positively (labeled as a, b, and c in FIG. 6A), thus indicating that HER2 status does not underlie the observed changes in gene expression pattern. Relative expression of Rb and p16ink4a is also examined, and mRNA levels show no significant alteration across the tumor specimens. This result is not unexpected, as relative Rb and p16ink4a mRNA levels are typically unaltered even in tumors with loss of heterozygosity at the RB locus and/or that score histologically negative for RB expression (e.g., in small cell lung carcinoma). These observations are consistent with the established observations that RB inactivation is frequently associated with regulation of protein function rather than loss of the RB gene itself in breast cancer.

Since one suggested mechanism for loss of RB function is attributed to excessive $G_1$ cyclin/CDK activity, relative $G_1$ cyclin mRNA levels are analyzed in the cohort. As shown, cyclin D1 levels did show a differential expression pattern, wherein a large number of tumors (43%) showed elevations in cyclin D1 and mRNA production. However, cyclin D1 status did not correlate with the RB gene expression signature, thus indicating that the major mechanism of RB inactivation in this tumor cohort is unlikely to result from enhanced cyclin D1 gene expression. Moreover, these data indicate that the RB signature is not a general consequence of cell-cycle aberrations. Cyclin E mRNA levels did show an inverse relationship with functional RB consistent with existing literature, and correlated with the high RB gene expression group. Together, these data indicate that the RB-deficient signature is specific and likely arises from functional inactivation of the tumor suppressor action.

Figure 6B:
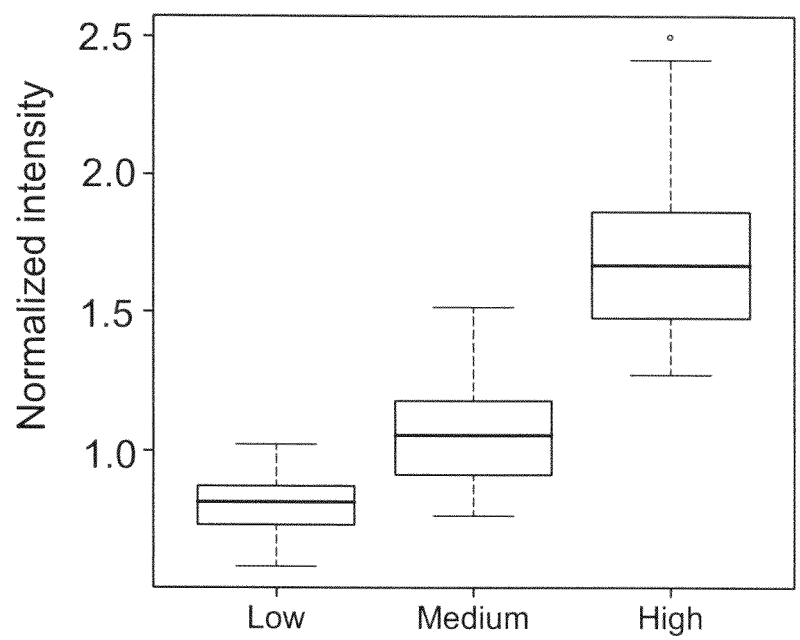
Figure 6C:
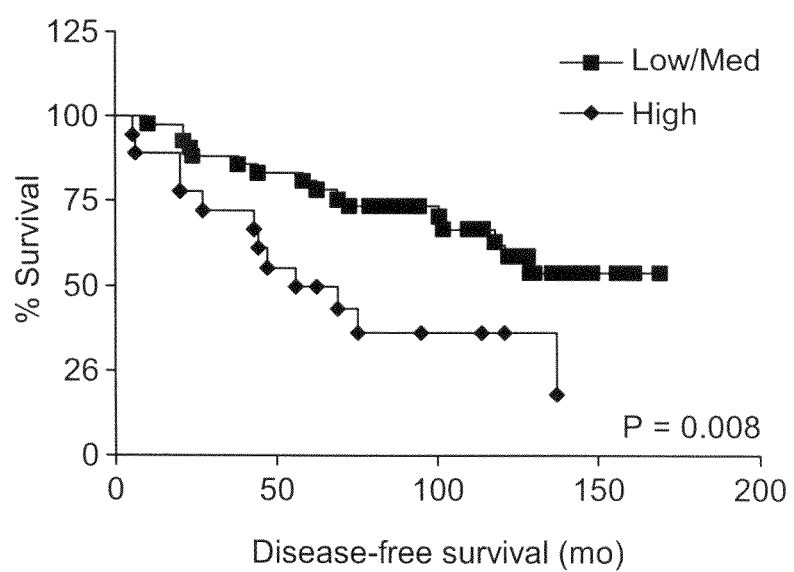

To address the importance of the RB deficiency signature on therapeutic response, patient outcome is examined. Recurrence data revealed that the patients in the "high" target gene group have an increased incidence of cancer recurrence (65%) relative to the patients in the other 2 groups (38%). The increased levels of RB/E2F target genes in this high group would suggest that these tumors are functionally disrupted for the RB pathway, and their poor response to Tam therapy would correspond with data described herein. The average expression levels of these 59 RB target genes in each of the 3 groups are quantitatively displayed as a box plot to reveal an approximate 3-fold increase in gene expression from the low to the high group (FIG. 6B). For each patient, the time to disease recurrence is known, and a recurrence-free survival curve is generated (FIG. 6C). Patients responded poorly to Tam in the high expression group, wherein the median recurrence-free survival is 62.5 months, and only 35% remained recurrence free. In contrast, patients in the low/medium RB target gene expression groups had an improved prognosis on Tam therapy, with greater than 62% remaining disease free. Thus, compromised control of the RB/E2F axis is associated with poor response to Tam in human breast cancer.

The RB tumor suppressor is functionally inactivated in a large fraction of human cancers. Traditionally, this event is associated with the genesis of cancer as opposed to the effect on the therapeutic response of a given tumor type. Here the influence of RB deficiency in the context of established breast cancer cells is evaluated and it is found that while attenuation of RB function did accelerate cellular and tumorigenic proliferation, it also has a profound influence on the response to key therapeutic modalities utilized in the treatment of breast cancer.

It is widely held that RB functions as a negative regulator of cell-cycle progression that is targeted at high frequency in human cancers by a myriad of mechanisms. The frequency of this event has led to the hypothesis that most cancers functionally inactivate RB during tumor progression. Such a model would suggest that although the RB protein is expressed in many tumor types, it is functionally inert due to upstream deregulation of RB phosphorylation. In this work, the influence of RB deficiency on several breast cancer cell lines is investigated. Knockdown of RB led to the enhanced expression of E2F target genes, suggesting that the RB protein present in MCF7 cells is at least partially functional. Subsequent analyses of cell-cycle progression and cellular proliferation indicates that, similar to what is observed in primary cells, knockdown of RB induces a modest proliferative advantage in MCF7, T47D, and Zr-75-1 cells. Strikingly, in MCF7 cells, RB deficiency also facilitates tumorigenic proliferation. Thus, while many mechanisms may attenuate the RB pathway sufficiently to promote tumorigenesis, many tumor lines retain sufficient RB activity to activate checkpoints when provoked, such that complete deficiency of RB can further enhance proliferation and alter tumor cell behavior.

Breast cancer, like all cancers, is a heterogeneous disease. In the case of ER-positive disease, Tam or similar antiestrogenic compounds are utilized to treat the cancer. However, many ER-positive patients develop resistance to antiestrogen therapy, and an alternative line of therapy such as either radiation or chemotherapy is required. It has been found in primary cells that the RB/E2F pathway plays an important role in mediating cell-cycle inhibition following exposure to such agents. In several breast cancer cell lines, we observe a similar dependence on RB/E2F function, as either the knockdown of RB or overexpression of E2F3 (MCF7 cells) enable bypass of the DNA damage checkpoint. Strikingly, this loss of checkpoint function increases the sensitivity of RB-deficient MCF7 cells or tumors to IR and CDDP, respectively. These findings are in agreement with prior studies in primary murine cells, where RB deficiency was found to enhance susceptibility to death following DNA damage, which was most likely due to deregulation of cell-cycle and proapoptotic genes. Thus, aberrations in RB, while uncoupling cell-cycle responses, lead to enhanced sensitivity to cytotoxic therapeutics that function by damaging DNA. This is clinically important for patients harboring either ER-negative or ER-positive Tam-resistant tumors. In addition, disruptions in the p53 pathway are known to occur in 20%-40% of breast cancers, although most frequently in ER-negative cases. Therefore, the influence of p53 function on DNA damage checkpoint response and sensitivity in MCF7 models is examined, and these analyses showed that while p53 does impact the DNA damage checkpoint, there is only a marginal effect on long-term sensitivity, as suggested in the literature. These data indicate that RB function modifies therapeutic response even in the absence of p53.

First-line therapy for ER-positive breast cancer exploits the estrogen dependence of these cells. Treatment of estrogen-sensitive ER-positive tumors with estrogen antagonists results in inhibition of tumor growth and corresponding tumor regression. However, up to 50% of ER-positive tumors fail to respond to such therapeutics. Here the influence of compromising the RB/E2F pathway on response to estrogen antagonists is determined. Cells with a disruption in this pathway fail to undergo cell-cycle inhibition following hormone therapy. However, unlike the situation with DNA-damaging agents, the RB-deficient breast cancer cells continue to proliferate in the presence of Tam. As a result, RB-deficient tumors continue to progress in the presence of Tam and thus fail therapy. However, RB deficiency only partially bypasses the requirement for estrogen. This finding is likely attributed to the complexity of estrogen signaling pathways, which cannot be fully recapitulated by RB deficiency. Such a supposition is supported by partial bypass that is observed with overexpression of Her2/Neu. Interestingly, although p53-deficient MCF7 cells are able to bypass the checkpoint to DNA damage therapy, the same is not evident following hormone ablation therapy. These data, combined with the observation that MCF7, T47D, and Zr-75-1 cells are all p16INK4a deficient yet display resistance to hormone therapy upon RB knockdown, suggest that the influence of RB on the response to antiestrogen therapy is not effectively recapitulated by other tumor suppressor pathways. Together, these findings have significant clinical impact, since nearly all of the patients whose tumors initially respond to Tam eventually develop cellular resistance.

The involvement of RB function in breast cancer therapy has not previously been examined. In human disease, disruption of the RB pathway occurs with relatively high frequency (>80%) and is often associated with poor prognosis. Since RB function can be disrupted via mechanisms that do not directly target the protein (e.g., point mutations) and deregulated E2F activity could similarly bypass Tam, the analyses of RB target genes results in an important determinant of Tam response. These RB target genes are defined based on RB genetic loss and induction of RB function in cells. As expected, this "signature" is largely consistent with genes that are also regulated by the E2F family of transcription factors. Consistent with such analyses having merit, it has been reported that high levels of the RB/E2F targets, cyclin A and cyclin E, correlate with Tam resistance. Furthermore, the high expression of RB target genes is associated with poor response to Tam in the context of monotherapy. Therefore, these clinical data indicate that disruption of the RB/E2F pathway plays a role in the progression of breast tumors to antiestrogen resistance. It could be reasoned that upregulation of RB/E2F targets, many of which are cell-cycle genes, could be associated with poor prognosis in general. However, in studies to define gene expression signatures in breast cancer survival, metastasis, and tumor grade, RB/E2F target genes have not been widely represented, except in highly specific subpopulations of patients. Interestingly, RB targets from our signature do consistently constitute a small subset of these gene lists and thus should be subject to further investigation, as they likely contribute not only to therapeutic bypass but disease severity and aggressiveness. In fact, aberrations in RB correspond with ER negativity in breast cancers, indicating that RB functional inactivation could be a crucial step in the progression to advanced disease. There are a myriad of mechanisms through which RB functional inactivation could occur to deregulate gene expression in breast cancer. Our studies suggest that cyclin D1 gene upregulation or protein overexpression fail to predict Tam response. This is consistent with several studies that have shown that cyclin D1 levels do not stringently correlate with Tam resistance. Although our studies are modeling immunohistochemical loss of RB, disruption of RB transcriptional repression can occur through additional mechanisms, for example, excessive cyclin E expression, expression of hyperactive (low-molecular-weight) cyclin E, loss of the CDK2 inhibitor p27kip1, or loss of the Brm SWI/SNF ATPase have been shown to compromise RB function in cancer cells. Together, these studies show that disruption of the RB/E2F axis has a deleterious influence on hormone therapy and can be utilized as a metric for informing therapeutic choice.

Materials and Methods

The MCF7, T47D, and Zr-75-1 cell lines are obtained from ATCC and propagated in DMEM containing 10% FS supplemented with 100 U/ml penicillin/streptomycin and 2 mM L-glutamine at 37° C. in air containing 5% $CO_2$. Cells are infected with adenovirus encoding either E2F3 or the lacZ gene as a control. Cells are infected with Ad-lacZ at a multiplicity of infection of 50, at which 95% of cells are infected (as determined by plaque assay in 293 cells) or with $2.7 \times 10^{11}$ virus particles/ml of Ad-E2F3 and cultured for 3 days prior to use. RB-knockdown or control MCF7 cells are created through transfection with either an shRNA plasmid directed against Rb (MSCV-Rb3C; targeted sequence: 5'-CGCATACTCCGGTTAGGACTGTTATGAA-3') (SEQ. ID. 1) or a control plasmid (MSCV donor) using FuGENE Transfection Reagent. Following selection with 2.5 μg/ml puromycin for 3-4 days, stable clones are isolated and characterized. Retrovirus encoding an shRB plasmid (MSCV-LMP Rb88; targeted sequence: 5'-GAAAGGACATGTGAACTTA-3') (SEQ. ID. 2) or control plasmid (MSCV donor) are utilized to create RB-knockdown or control Zr-75-1 and T47D cell lines. Following selection with 2.5 μg/ml puromycin for 3-4 days, polyclonal cell lines are characterized. MCF7 donor 1 and MCF7siRb28 cells are infected with retrovirus encoding LXSN or LXSN-p53dd, selected with 900 μg/ml G418 for 7 days, and pooled for characterization.

To study the effect of estrogen depletion, cells are cultured for 72 hours in phenol red-free DMEM supplemented with 10% CDT serum with addition of $10^{-9}$ M 4-HydroxyTam or $10^{-6}$ M ICI where indicated. Cell growth assays are performed by trypsinizing cells and counting by trypan blue exclusion every 3 days.

Cells are harvested by trypsinization and lysed in RIPA buffer. Equal amounts of protein, as determined by Bio-Rad DC assay, are resolved by SDS-PAGE. Specific proteins are detected by standard immunoblotting procedures using the following primary antibodies: p16INK4a (F-12; 1:500 dilution), cyclin D1 (H295), PCNA (pc10), cyclin E (HE12), cyclin A (C-19), MCM7 (141.2), E2F3 (C-18), cdk4 (H-22), lamin B (M-20), p21 (C-19), p53 (Ab-6; 1:500 dilution), RB phospho ser 780 (9307S; 1:500 dilution) and anti-RB (G3-245; 1:100 dilution). Immunofluorescence staining for RB is performed on cells growing on coverslips by fixing them in 3.7% formaldehyde in PBS for 10 minutes. Cells are permeabilized in 0.3% Triton X-100 in PBS for 20 minutes and blocked in 5% fetal goat serum in PBS for 1 hour. Cells are incubated in blocking solution with anti-RB antibody (G3-245; 1:25 dilution) for 1 hour at 37° C. followed by PBS washing and incubation with Alexa 488 secondary:antibody (1:100) and counterstained with DAPI.

Cells treated with IR are exposed to $^{137}$Cs (dose rate: 0.67 Gy/min) at room temperature in tissue culture media. Culture with clinical grade CDDP for 18 hours is performed for all CDDP treatments. For all proliferation studies, cells are labeled with BrdU for 10 hours or 5 hours for LXSN/LXSN-p53dd infected cells, and BrdU immunofluorescence is performed as previously described. All BrdU results are expressed as a percentage of untreated control cells set to 100%, unless otherwise noted.

Five- to 8-week-old female ovariectomized athymic nude mice are anesthetized, and an E2 pellet (1.7 mg/pellet, 90-day release) or placebo is surgically implanted in the back. Following implantation, 200 μl of a PBS- and phenol red-free Matrigel matrix basement membrane, solution (3:1) containing 2×10$^6$ cells is injected subcutaneously into the flank, or contralaterally where noted. Tumor volume is measured with calipers every 4 days using the equation V=0.52 (width)$^2$ ×(length). In the therapeutic studies, when tumor volume reaches 100-120 mm$^3$, animals are placed into 1 of 3 therapeutic groups (each group containing at least 6 animals): control animals retaining the estrogen pellet, antiestrogen-treated animals, or CDDP-treated animals. Animals in the antiestrogen treatment group are anesthetized, the estrogen pellet is surgically removed, and a Tam pellet (5 mg/pellet, 60-day release) implanted. The CDDP-treated animals receive 5 mg/kg CDDP injected i.p. on a q4dx5 schedule (every 4 days for 5 courses). All animals are injected i.p. with 150 mg/kg BrdU (Sigma-Aldrich) 1 hour prior to euthanization. Xenograft tumors are weighed and fixed in 10% neutral buffered formalin, paraffin embedded, and cut into 5-ÿm sections. For immunohistochemical staining, sections are deparaffinized in xylene and rehydrated through a graded series of ethanol/water solutions. A BrdU detection kit is utilized as recommended by the manufacturer. BrdU incorporation is scored in a blinded manner, and at least 500 cells per section are counted from several random fields.

The foregoing description of various embodiments and principles of the invention has been presented for the purposes of illustration and description. It is not intended to be exhaustive or to limit the inventions to the precise forms disclosed. Many alternatives, modifications, and variations will be apparent to those skilled the art. Moreover, although multiple inventive aspects and principles have been presented, these need not be utilized in combination, and various combinations of inventive aspects and principles are possible in light of the various embodiments provided above. Accordingly, the above description is intended to embrace all possible alternatives, modifications, aspects, combinations, principles, and variations that have been discussed or suggested herein, as well as all others that fall within the principles, spirit and scope of the inventions as defined by the claims.

What is claimed is:

1. A method of managing treatment of a human having an (ER)-positive human breast cancer tumor, the method comprising:
   a) obtaining a sample of the tumor from the human;
   b) determining an average level of expression of a plurality of genes regulated by retinoblastoma tumor suppressor (RB) in the sample by determining the average level of expressed RNA of the plurality of genes regulated by RB, wherein the plurality of genes regulated by RB consists of: RAD21, BRCA1, ECT2, KIF11, SMC4L1, TOPBP1, STK6, KIF20A, CDC25C, CCNB1, CDC20, CDCA8, KIF2G, BIRC5, CDC45L, CDCA3, PRC1, CCN82, MK167, RAD51, CDCA5, BRRN1, TTK, KIF23, BUB1, CENPA, CCNA2, RRM2, TRIP13, EZH2, MAD2L1, TOP2A, RAD51AP1, TYMS, PCNA, HMGB2, FEN1, NEK2, CKS2, CHEK1, CDC6, GMNN, FIGNL1, TMPO, TCF19, LIG1, MCM2, MCM3, BRCA2, SMC2L1, PRIM1, RFC5, CDK2, CDCA7, PLTP, and TYRO3;

c) determining whether the tumor is resistant to antiestrogen therapy by comparing the average level of expression of the plurality of genes regulated by RB in the sample with an average level of expression of the plurality of genes regulated by RB in a control, wherein the control represents a tumor responsive or non-responsive to the antiestrogen therapy, and wherein the antiestrogen therapy comprises tamoxifen; and d) managing the treatment of the human by (i) treating the human with antiestrogen therapy as a first-line therapy where the tumor is not resistant to the antiestrogen therapy, and (ii) treating the human with DNA-damaging therapy as a first-line therapy where the tumor is resistant to the antiestrogen therapy.

2. The method of claim 1, wherein the average level of expressed RNA is determined by microarray analysis, quantitative polymerase chain reaction, or a combination thereof.

3. The method of claim 1, wherein the tumor is resistant to antiestrogen therapy when:
the sample has an average higher expression of the plurality of genes regulated by RB as compared with a control representing a tumor responsive to the antiestrogen therapy, and
the sample has an average similar level of expression of the plurality of genes regulated by RB as compared with a control representing a tumor resistant to the antiestrogen therapy.

4. The method of claim 3, wherein the higher expression is at least about 2 fold higher in the sample as compared with the control.

5. The method of claim 3, wherein the average higher expression of the plurality of genes regulated by RB is from about 1.5 to 2.0 normalized intensity.

6. The method of claim 1, wherein the treating with antiestrogen therapy comprises treating with tamoxifen.

7. The method of claim 1, wherein the DNA-damaging therapy comprises radiation or chemotherapy.

8. The method of claim 1, wherein a human having a sample with an average higher expression of the plurality of genes regulated by RB as compared with a control representing a tumor responsive to the antiestrogen therapy indicates that the human will have an increased incidence of cancer recurrence relative to a human having a sample with an average low or average medium expression of the plurality of genes regulated by RB as compared with a control representing a tumor responsive to the antiestrogen therapy.

9. The method of claim 8, wherein the increased incidence of cancer recurrence is about 65%.

\* \* \* \* \*

```
                          SEQUENCE LISTING

<160> NUMBER OF SEQ ID NOS: 2

<210> SEQ ID NO 1
<211> LENGTH: 28
<212> TYPE: DNA
<213> ORGANISM: Homo sapiens

<400> SEQUENCE: 1
cgcatactcc ggttaggact gttatgaa                                      28

<210> SEQ ID NO 2
<211> LENGTH: 19
<212> TYPE: DNA
<213> ORGANISM: Homo sapiens

<400> SEQUENCE: 2
gaaaggacat gtgaactta                                               19
```